(12) United States Patent
Planard-Luong

(10) Patent No.: US 10,238,866 B2
(45) Date of Patent: Mar. 26, 2019

(54) IONTOPHORESIS DEVICE WITH MULTI-ELECTRODE END PIECE

(71) Applicant: L'OREAL, Paris (FR)

(72) Inventor: Thi Hong Lien Planard-Luong, Bures sur Yvette (FR)

(73) Assignee: L'OREAL, Paris (FR)

( * ) Notice: Subject to any disclaimer, the term of this patent is extended or adjusted under 35 U.S.C. 154(b) by 83 days.

(21) Appl. No.: 15/500,195

(22) PCT Filed: Jul. 16, 2015

(86) PCT No.: PCT/EP2015/066326
§ 371 (c)(1),
(2) Date: Jan. 30, 2017

(87) PCT Pub. No.: WO2016/016014
PCT Pub. Date: Feb. 4, 2016

(65) Prior Publication Data
US 2017/0252557 A1    Sep. 7, 2017

(30) Foreign Application Priority Data

Jul. 29, 2014 (FR) .................................... 14 57332

(51) Int. Cl.
*A61N 1/30* (2006.01)
*A61N 1/32* (2006.01)
(Continued)

(52) U.S. Cl.
CPC .............. *A61N 1/303* (2013.01); *A61B 18/14* (2013.01); *A61B 18/18* (2013.01); *A61M 35/003* (2013.01);
(Continued)

(58) Field of Classification Search
CPC .... A61N 1/303; A61N 1/0428; A61N 1/0432; A61N 1/30; A61N 1/044; A61N 1/325;
(Continued)

(56) References Cited

U.S. PATENT DOCUMENTS 4,323,652 A    4/1982  Baudry et al.
4,618,590 A    10/1986 Baudry
(Continued)

FOREIGN PATENT DOCUMENTS

CN      200951261 Y   9/2007
CN      101532190 A   9/2009
(Continued)

OTHER PUBLICATIONS

Fluroplastics by Jiri Drobny, p. 12, Table 8 (available online Jun. 20, 2018 at https://books.google.com/books?id=hyulhAiqUqoC&pg=PA12&dq=electrical+resistivity+of+ptfe&hl=en&sa=X&ved=0ahUKEwitqYr2kePbAhVPrlkKHX4kAGsQ6AElJzAA#v=onepage&q=electrical%20resistivity%20of%20ptfe&f=false.*
(Continued)

*Primary Examiner* — Amber Stiles
(74) *Attorney, Agent, or Firm* — The Marbury Law Group, PLLC

(57) ABSTRACT

The invention relates to an end piece intended for equipping a device for cosmetic treatment of keratin materials with an electric current, the end piece comprising an application member (6) comprising an electrode (1) and a counter electrode (2), said electrode (1) and counter electrode (2) being separated from one another by an electrically insulating zone (3).

18 Claims, 2 Drawing Sheets

(51) Int. Cl.
    *A61B 18/14* (2006.01)
    *A61B 18/18* (2006.01)
    *A61M 35/00* (2006.01)
    *A61N 1/04* (2006.01)
    *A61B 18/00* (2006.01)

(52) U.S. Cl.
    CPC ............ *A61N 1/044* (2013.01); *A61N 1/325* (2013.01); *A61B 2018/0047* (2013.01); *A61B 2018/00083* (2013.01); *A61B 2018/00714* (2013.01); *A61B 2018/00791* (2013.01); *A61B 2018/1467* (2013.01)

(58) Field of Classification Search
    CPC ............... A61B 18/18; A61B 18/14; A61B 2018/00791; A61B 2018/1467; A61B 2018/0047; A61B 2018/00083; A61B 2018/00; A61B 2018/00714; A61M 35/003
    See application file for complete search history.

(56) References Cited

U.S. PATENT DOCUMENTS

| | | | |
|---|---|---|---|
| 4,699,827 A | 10/1987 | Baudry | |
| 5,443,441 A | 8/1995 | De Claviere | |
| 6,157,858 A | 12/2000 | Gross et al. | |
| 6,684,107 B1* | 1/2004 | Binder | A61N 1/32 607/145 |
| 6,702,792 B2 | 3/2004 | Nakamura et al. | |
| 6,766,192 B1 | 7/2004 | D'Africa et al. | |
| 7,069,088 B2 | 6/2006 | Lehtoluoto | |
| 7,477,939 B2 | 1/2009 | Sun et al. | |
| 8,321,009 B2 | 11/2012 | Rosemberg | |
| 8,343,147 B2 | 1/2013 | Rosemberg | |
| 8,791,173 B2 | 7/2014 | Kotake et al. | |
| 2002/0010414 A1* | 1/2002 | Coston | A61B 5/14514 604/20 |
| 2003/0041538 A1* | 3/2003 | Ting | E06B 3/4609 52/204.5 |
| 2004/0006374 A1* | 1/2004 | Mondin | A61N 1/30 607/3 |
| 2004/0267189 A1 | 12/2004 | Mayor et al. | |
| 2005/0123565 A1 | 6/2005 | Subramony et al. | |
| 2007/0088392 A1 | 4/2007 | Skiba et al. | |
| 2008/0195181 A1* | 8/2008 | Cole | A61N 1/328 607/74 |
| 2009/0143761 A1 | 6/2009 | Cantor et al. | |
| 2010/0057147 A1 | 3/2010 | Fassih et al. | |
| 2010/0274329 A1* | 10/2010 | Bradley | A61N 1/328 607/90 |
| 2011/0086946 A1 | 4/2011 | Kotake et al. | |
| 2013/0253412 A1 | 9/2013 | Yanaki et al. | |
| 2015/0088050 A1* | 3/2015 | Chang | A61N 1/328 604/20 |

FOREIGN PATENT DOCUMENTS

| | | |
|---|---|---|
| CN | 203483023 U | 3/2014 |
| EP | 0016498 A1 | 10/1980 |
| EP | 0168849 A1 | 1/1986 |
| EP | 2111889 A1 | 10/2009 |
| EP | 2430945 A2 | 3/2012 |
| FR | 2917299 A1 | 12/2008 |
| GB | 2372705 A | 9/2002 |
| JP | H11-47284 A | 2/1999 |
| JP | 2009-179915 | 8/2009 |
| WO | 2005/004981 A2 | 1/2005 |
| WO | 2008/057640 A2 | 5/2008 |
| WO | 2009/144684 A2 | 12/2009 |
| WO | 2009/150972 A1 | 12/2009 |
| WO | 2012/106735 A2 | 8/2012 |
| WO | 2016/016015 A1 | 2/2016 |

OTHER PUBLICATIONS

International Search Report for PCT/EP2015/066326, dated Sep. 8, 2015.
International Search Report for PCT/EP2015/066330, dated Sep. 23, 2015.
Singh, J. et al., "Topical Iontophoretic Drug Delivery: Pathways, Principles, Factors, and Skin Irritation," Medicinal Research Reviews, vol. 16, No. 3, (1996), pp. 285-296.
First Chinese Office Action for counterpart Application No. 201580041105.4, dated Jul. 6, 2018, (no translation available).

* cited by examiner

IONTOPHORESIS DEVICE WITH MULTI-ELECTRODE END PIECE

CROSS REFERENCE TO RELATED APPLICATIONS

This is a national stage application of PCT/EP2015/066326, filed internationally on Jul. 16, 2015, which claims priority to French Application No. 1457332, filed on Jul. 29, 2014, which are incorporated by reference herein in their entireties.

The present invention relates to devices for carrying out a cosmetic treatment of keratin materials, in particular of the skin, the scalp or the hair.

Throughout the text, the expression "comprising a" should be interpreted as being synonymous with "comprising at least one".

The term "device" is understood to mean a set of parts constituting an appliance, this appliance not being an "article".

An "article" is a mask, a patch, a pad, a strip or a bandage capable of being applied to human keratin materials.

In particular, the device according to the invention comprises an end piece free of nonwoven material.

Notably, the device according to the invention comprises a hand piece that bears the end piece. The hand piece is moved by the user over the body surface to be treated.

The expression "cosmetic product" is understood to mean any composition as defined in Council Directive 93/35/EEC of 14 Jun. 1993.

It is known that the application of an electric current to the skin can promote the penetration of active agents.

It is thus known to treat human keratin materials using iontophoresis devices (J. Singh, K. S. Bhatia, Topical iontophoretic drug delivery: pathways, principles, factors and skin irritation, Med. Res. Rev., vol. 16, no. 3, 285-296, 1996).

Iontophoresis allows the diffusion of active agents through the skin by virtue of electrical stimulation in a non-invasive manner. The current applied may be adjustable in terms of intensity and direction (anodel or cathodal). The transcutaneous diffusion of the molecules via iontophoresis is based on two principles, namely electrorepulsion and electroosmosis.

Electrorepulsion is the migration of an ionized molecule by repulsion of charges of the same sign. Thus, if a substance is negatively charged, it will diffuse through the skin at the cathode (−).

Electroosmosis is the migration of a molecule, even a non-ionized molecule, by entrainment associated with the flow of water from the anode to the cathode during iontophoresis. The migration is due in particular to the negative charge of the skin. Under the effect of a current, the water or a solvent entrains dissolved substances as it migrates.

The electric current can be applied to the skin by means of an end piece. For large surfaces of the body or of the facial cheek, the end piece may be large. In areas that are more difficult to access, the end piece may take the form of a small head that is easier to bring into contact or to move.

In order to increase the effectiveness of the iontophoresis, it is necessary to develop specific devices which optimize the penetration of the active agents through the skin.

It is already known to use an iontophoretic device provided with a massaging end piece for generating a massage that facilitates this penetration.

By way of illustration, the documents EP 2 430 945 and EP 2 111 889 describe a device for treating the contour of the eye by way of a metal ball connected to the electrode and an integrated cosmetic composition reservoir.

The patent GB 2 372 705 A describes an iontophoretic device having electrodes made of ABS plastic metallized by a corrosion-resistant metal. The reservoir is also connected to the electrode in order to ionize the formulation.

The U.S. Pat. No. 6,766,192 B1 describes an iontophoretic device having a ball fixed to a tube of cream.

The professional TMT® device sold by the company Bodyesthetic uses an iontophoretic device provided with a rotary ball made of stainless steel.

The i-beauty Gun® device sold by AAMS (Anti-Aging Medical Systems) outputs a current via a probe of the roller type, wherein the deposition of product is regulated on the basis of the impedance measured between an electrode and the skin. With this device, the quantity of product delivered is controlled by an electronic system with a view to reducing the contact impedance with the skin.

However, in all the currently known devices, the penetration efficiency is not therefore optimized.

Safety standards require that the total current passed through the body (especially when it passes through sensitive organs such as the heart) must be limited to less than 5 mA. Therefore, it is sought to control the inter-electrode current so that it does not go too deep but remains effective for pushing the active agents into the skin.

It is desirable to improve the iontophoretic end pieces for a more effective penetration, greater safety and a uniform treatment result over the entire surface treated.

There is thus a need for a device for cosmetic treatment with an electric current which can ensure greater effectiveness than the known devices and which can be used in complete safety.

There is a need to further increase the amount of active agents penetrating through the skin using an iontophoretic device, while respecting the safety regulations.

There is also a need to increase the effectiveness of the iontophoretic devices, irrespective of the targeted cosmetic treatment.

There is additionally a need to provide an iontophoretic device that enables the uniform application of a cosmetic composition containing an active principle.

The device must additionally be easy to manufacture and to handle.

In particular, there is a need to develop novel devices:

that can be used both with a direct current, and with a pulsating current or else with a current consisting of a direct component and a pulsating component, that ensure the current passes into the skin and not only to the surface thereof, that prevent the current from penetrating too deeply beneath the skin, that increase the overall amount of current, while keeping the intensity constant for a wide treatment area.

The invention aims to resolve all or some of the aforementioned needs and also to further improve the devices for cosmetic treatment of human keratin materials with an electric current.

For this purpose, the invention proposes the integration of electrically insulating zones between the electrodes on the same end piece. The depth of the currents migrating through the skin is thus controlled. They are rendered electrically independent.

When the end piece is moved over the face, the pressure exerted at certain locations thereof is greater than at other locations. However, it is observed that in the region where the skin is subjected to a high pressure, the electrical conductivity of the skin decreases. The electrically insulating zone ensures a safe and firm contact on the skin.

In addition, it generates a discontinuity of the electrical conductivity at the surface and in the superficial layer of the skin located between the electrodes. The current is thus constrained to pass through the skin. It cannot remain at the surface thereof.

Finally, a cosmetic composition may be trapped around the electrically insulating zone. The active agents to be transported remain in the vicinity of the electrodes. The device is particularly effective.

More specifically, one subject of the invention is an end piece intended for equipping a device for cosmetic treatment of keratin materials with an electric current, the end piece comprising an application member comprising an electrode and a counter electrode, said electrode and counter electrode being separated from one another by an electrically insulating zone.

Another subject of the invention is a device for cosmetic treatment of keratin materials with an electric current, the device being equipped with an end piece comprising an application member comprising an electrode and a counter electrode, said electrode and counter electrode being separated from one another by an electrically insulating zone.

Owing to the electrically insulating zone, the current does not pass over the surface of the skin by taking the shortest path between the electrode and the counter electrode. On the contrary, it is made to bypass the electrically insulating zone by being diverted to inside the skin.

In addition, it is possible to judiciously choose the electrically insulating zone in order to modify/obtain particular characteristics, depending on the desired insulation. The invention thus proposes a wide range of end pieces having electrical characteristics that can be adapted to the targeted treatment or to the area of the face treated.

The general principle of the invention is the insertion of an electrically insulating zone between the electrode and the counter electrode. The positioning of the electrically insulating zone is optimized in order to control the depth of currents through the skin. It can be compared with the multipolar radiofrequency principle.

Advantageously, the electrically insulating zone is designed to prevent the diffusion of a cosmetic composition between the electrode and the counter electrode.

It is a zone that is impermeable to fluids or else a zone that is leaktight with respect to fluids.

Preferably, the electrically insulating zone defines a wall, the height of which is greater than or equal to the thickness of the electrode and of the counter electrode.

Thus, the effectiveness of the electrically insulating zone is increased.

GENERAL DEFINITIONS

According to the invention, an "electrode" is understood to be a positively charged electrode (anode) or a negatively charged electrode (cathode). This electrode is generally disposed on the external surface of the device so as to come into direct contact with the keratin materials. However, the electrode may also be inserted into the external wall of the device. In this case, it does not come into direct contact with the keratin materials. In general, the electrode is in contact with the area to be treated.

Throughout the text, the term "electrode" means an insulated electrode. An electrode may be, for example, in the form of a ball or stud. A "counter electrode" is understood to be a negatively charged electrode (cathode) or a positively charged electrode (anode). The charge of the counter electrode is opposite to that of the electrode.

A "power supply system" is understood to be an electrical assembly that is able to induce a potential difference between the electrodes and the counter electrode.

Structure of the Electrically Insulating Zone

Preferably, the electrically insulating zone defines a wall with:
a height greater than or equal to the thickness of the electrode and of the counter electrode,
a maximum width less than or equal to the distance between the electrode and the counter electrode.

The electrically insulating zone may have any shape. For example, it may have a square, rectangular, polygonal, elliptical or oval cross section.

Preferably, the electrically insulating zone forms a bar, an insulating plate or an insulating cylinder.

The electrically insulating zone may form a relief at the surface of the end piece, especially if the electrodes come into contact with the skin. For example, it may form protruding beads or ribs. The relief is, preferably, oriented parallel to the longitudinal axis of the electrode and of the counter electrode.

The electrically insulating zone may also completely or partially fill a rib or a groove extending, preferably, parallel to the longitudinal axis of the electrode and of the counter electrode.

Parameters of the Electrically Insulating Zone

The electrically insulating zone has an electrical conductivity of zero or almost zero and an infinite resistance ($\infty\Omega$).

The electrically insulating zone is also defined by its permittivity and by electric strength.

Advantageously, the electrically insulating zone has an electrical conductivity of less than $10^{-6}$ S·m$^{-1}$, preferably of less than $10^{-12}$ S·m$^{-1}$.

Permittivity

The permittivity or dielectric constant of an insulator is expressed relative to that of air (equal to that of a vacuum). It is represented by the letter epsilon $\varepsilon$ and expressed in picofarads/meter.

The vacuum permittivity is equal to:

$$\varepsilon_0 = 8.854187 \cdot 10^{-12} \text{ F·m}^{-1}$$

The absolute permittivity of a material is the product of its relative permittivity (see table below) multiplied by the vacuum permittivity according to the formula: $\varepsilon = \varepsilon_0 \times \varepsilon_R$ For Teflon it is 18.6 pF/m.

Permittivity and Dielectric Strength of Several Insulators

These values are approximate and may vary markedly as a function of the frequency, of the temperature, of the hygrometry or even of the atmospheric pressure.

Permittivity is also referred to as dielectric constant (symbol $\varepsilon_r$).

The dielectric strength is in kV/mm

| Insulator | Relative permittivity $\varepsilon_r$ | Dielectric strength (kV/mm) |
| --- | --- | --- |
| Dry air | 1 | 4 |
| Rubber | 4 | 15 |
| Silicone rubber | 4.2 | — |
| Cardboard | 4 | 10 |
| Kapton ® | | 110 |
| Mica | 6 | 70 |
| Paper | 2 | 6 |
| Paraffin | 2.2 | — |
| PVC | 5 | 20 |

-continued

| Insulator | Relative permittivity $\varepsilon_r$ | Dielectric strength (kV/mm) |
| --- | --- | --- |
| Plexiglas | 3.3 | — |
| Polyester | 3.3 | — |
| Polyethylene | 2.25 | 18 |
| Polypropylene | 2.2 | — |
| Polystyrene | 2.4 | 24 |
| Polycarbonate | 2.9 | 30 |
| Steatite | 5.8 | — |
| Styroflex | 2.5 | — |
| Teflon | 2.1 | 17 |
| Glass | 5 to 7 | 10 |
| Glass-epoxy laminate | 5 | 20 |

Advantageously, the electrically insulating zone is defined by a relative permittivity of greater than 0.5, preferably greater than 1, and preferably greater than 2.5.

Advantageously, the electrically insulating zone is defined by an electric strength of greater than 3 kV/mm, preferably greater than 4 kV/mm, and preferably greater than 20 kV/mm.

These values are optimal for obtaining an optimal electrical insulation between the electrode and the counter electrode.

Preferably, the electrically insulating zone comprises a material selected from electrically insulating polymers, electrically insulating ceramics or air.

Dimensions

The electrically insulating zone may have a width of between 1 and 10 mm, for example between 2 and 5 mm.

The electrically insulating zone may have a thickness of between 0.2 and 5 mm, and preferably between 1 and 3 mm.

The electrically insulating zone may be straight and/or curved. Advantageously, the electrically insulating zone may take the form of a straight strip.

Electrically Insulating Polymers

Preferably, the electrically insulating zone comprises a material selected from insulating thermoplastic materials, insulating thermosetting materials, insulating silicones, insulating thermoplastic elastomers, polyester-based or polyether-based insulating thermoplastic polyurethanes or PVC-based insulating thermoplastic elastomers.

The electrically insulating zone advantageously comprises the following insulating thermoplastic materials: polyamides (PA), polyolefins or polyalkenes (for example polyethylene PE, polypropylene PP, polymethylpentene PMP, polybutene PB-1, polyethylene terephthalate PET), styrene polymers (for example, polystyrene PS, expanded polystyrene EPS, acrylonitrile butadiene styrene terpolymer ABS), polyacrylics (polymethyl methacrylate PMMA) or else vinyl polymers (for example polyvinyl methyl ether PVME, polyvinyl acetate PVAc, polyvinyl chloride PVC).

Alternatively, the electrically insulating zone advantageously comprises the following insulating thermosetting materials: polyurethanes (PU) originating from the reaction of an isocyanate with hydroxylated groups in order to form a flexible open-cell foam suitable for contact with the skin.

Alternatively, inorganic polymers, the main chain of which does not comprise carbon atoms, are advantageously used as constituent material of the electrically insulating zone, especially polysiloxanes or silicones in common parlance. Some examples of the silicones used are polydimethylsiloxane (PDMS), silicone rubber comprising methyl and phenyl groups (PMQ), silicone rubber comprising methyl, phenyl and vinyl groups (PVMQ) or else silicone rubber comprising methyl and vinyl groups (VMQ).

The material constituting the separation zone may also advantageously be selected from insulating thermoplastic elastomers TPE, such as thermoplastic styrene elastomers (for example butadiene and styrene copolymers SBS and ethylene, butylene and styrene copolymers SEBS), thermoplastic polyurethanes TPU based on polyester (AU) or based on polyether (EU), and thermoplastic elastomers based on PVC (TPE/PVC).

The material constituting the electrically insulating zone may also be an ink, for instance that described in WO 2009150972, EP-A-0 016 498 or EP 0 168 849.

The material constituting the electrically insulating zone may be deposited on the application member by pressurized jet followed by drying and evaporation of the solvents. The material constituting the electrically insulating zone may be chemically impregnated on the application member.

Electrical Parameters

The electrical power source may comprise any non-rechargeable battery or any storage battery. The potential difference between the electrodes is for example between 1.2 V and 24 V, preferably between 1.2 and 10 V. If appropriate, the passage of the current can create spot heating.

At an equivalent current density, the device can in particular deliver a current density, at the skin, of preferably less than or equal to 0.500 mA/cm$^2$, for example between 0.01 mA/cm$^2$ and 0.500 mA/cm$^2$, for example between 0.01 mA/cm$^2$ and 0.20 mA/cm$^2$.

The Various Types of Currents

It is possible to use a direct current, an alternating current or a pulsating current to power the device according to the invention.

Preferably, the end piece is designed to be powered by a sequential current.

The sequential current is obtained by installing a switch. A current switching device, in other words a switch, is installed with the generator. This switch makes it possible to change the active state of the current sent to each compartment. Specifically, the current is sent in sequence to each compartment. Each sequence lasts between 1 second and 1 minute, preferably between 1 second and 10 seconds.

Advantageously, the end piece is designed so that the user can change the polarity of the current.

Thus, the device enables, at will, extraction of impurities from the body area, care of the body area or makeup of the body area.

Electrodes

The electrodes may have a visible free surface allowing them to come into direct contact with the skin.

The electrode may be flat, for example in the form of a flat disc, array or polygon.

The electrode may form an array.

The electrode may be porous. The electrodes may have various shapes and for example a surface intended to come into contact with the skin which is outwardly convex, outwardly concave, or flat. Preferably, the electrodes are smooth so as not to hurt the skin.

The electrodes may be formed by two spheres or rollers, which may or may not be able to rotate in respective housings.

The electrode may be hollow, being formed for example by stamping or bending an electrically conductive metal sheet.

Materials able to be used to produce the electrodes

The material(s) forming the electrodes may be identical or different.

At least one electrode may comprise, for example:
a metal (chromium, stainless steel), for example,
a noble metal (gold, titanium) which is inert with respect to the composition,
a metal plated with a noble metal,
an alloy,
a composite material (plastic material loaded with carbon microfibres),
a conductive woven fabric,
a conductive nonwoven fabric,
a polymer material rendered conductive,
a fibrous material,
conductive polymeric fibres, for example as described in the publication CN101532190,
carbon fibres, for example as described in the publication JP2009179915,
silicones rendered conductive by the addition of conductive fillers such as silver, copper or carbon. Such silicones are supplied, for example, by the companies Saint Gobain, Plastics Performance and Aquitaine Caoutchouc 2000,
conductive metallic fabrics, supplied for example by the companies Utexbel and Cousin Biotech,
carbon-loaded vinyl, supplied for example by the companies Copema and Rexam,
electrosurgical plates, supplied for example by the companies Copema and 3M,
intrinsically conducting polymers, supplied for example by the company Paniplast.

The "active surface of an electrode" is understood to mean the surface of an electrode in contact with the body area, when the application member is in place on said body area.

The "active surface of a compartment" is understood to mean the surface of the compartment in contact with the body area, when the application member is in place on said body area.

Cosmetic Composition

The cosmetic composition may be deposited directly on the area to be treated by the user.

The cosmetic composition may also be housed in a reservoir of the device.

The active principle is, preferably, charged. The term "charged" is understood to mean any active principle present at least partially in ionic form, the ions of which have an either positive or negative net charge, capable of ensuring their mobility within the composition under the effect of an electric field. Thus, the active agent is directly subjected to the attraction or repulsion of the electrodes.

Advantageously, the cosmetic composition is selected from care, washing, purifying, exfoliating, desquamating, massage, slimming, makeup, makeup removal, cleansing or bleaching compositions.

More advantageously, the cosmetic composition is in the form of an aqueous solution, an oil, an emulsion, a powder or a gel.

Irrespective of the embodiments considered, the device may exert an action on the skin via iontophoresis and/or electroosmosis.

The composition may comprise a composition for activating an unactivated active principle, for example in freeze-dried form. In this case, the composition may be free of a charged active principle. The composition may comprise a solvent having positively and negatively charged species, for example an ionic aqueous solution or an aqueous solution of deionized water or else a solution of NaCl.

It is also possible that the user applies an activation composition, for example a solvent, to the application member. For example, the user may apply running water, when no water is provided within one and the same packaging with the device.

In order to bring the application member and the activation composition into contact, the user may pour the composition onto the application member. The latter is, for example, present in a pouch or tray enabling the composition to be poured thereon. As a variant, the user may apply the composition to the skin then apply the application member on top.

Electrochemical Reaction

Generally, when it is sought to administer an active principle using the mask according to the invention, said active principle has the same polarity as the electrode. For example, the compounds containing active principles of positive polarity/charge, such as vitamin A, tocopheryl acetate or other active principles of positive charge/polarity, may be combined with an electrode of positive polarity.

The compounds containing active principles of negative polarity/charge such as retinyl palmitate, tocopherol or mandelic acid may, for their part, be combined with an electrode of negative polarity.

Supplementary Functions

The device may comprise one or more treatment modules which can be activated selectively, for example it is conceivable to subject the end piece to light, to a source of heat, or even to vibrations, as will be explained in detail below.

i) Source of Light

According to the invention, the device advantageously comprises a source of light.

The source of light may be, for example, at least one LED, as described in the documents FR-A-2 917 299, US-A-2010/274329 or WO-A-2008/057640.

ii) Source of Heat

According to the invention, the device advantageously comprises a source of heat.

In this case, it is possible to modify the temperature of the external surface of the end piece and/or of the region treated and/or to transmit energy to the external surface of the end piece and/or to the region treated.

The device may comprise for example a heating resistor or a thermoelectric element or an infrared source which is positioned under the end piece.

Preferably, the source of heat comprises an infrared source or a resistor.

The device may comprise a heating module and be configured to heat the external surface of the end piece to a predefined temperature, for example to a temperature of between 35° C. and 45° C. In the case of a device comprising a heating module, the heating surface can reach a temperature of 10° C. to 35° C. greater than room temperature, preferably of 15° C. to 25° C. greater in heating mode. The power delivered by the heating module may be between 0.25 and 10 W, preferably between 0.5 and 5 W.

More preferably, the source of heat is housed entirely inside the device.

The resistor may be connected to a board by two insulated connectors, using for example the location of the switches.

The infrared source may be integrated into the body of the device, such as the handle. The external part of the device, for example a shell, can serve to guide the infrared radiation towards the end piece.

The electrical circuit may comprise at least one electronic switch which is connected in series with the heating member and makes it possible for example to supply it with power at the desired ratio.

Creation of the Separation Zone

According to one embodiment of the invention, the process for creating the electrically insulating zone comprises the steps consisting in:

providing an application member, positioning the electrode and the counter electrode on the application member, defining the size and the geometry of the electrically insulating zone, optionally, marking the electrically insulating zone with a boundary, in particular with a mould, choosing an electrically insulating polymer, the melting point of which is markedly below the melting point of the constituent material of the application member, depositing the electrically insulating polymer in the molten state at the boundary, allowing the electrically insulating polymer to cure by cooling down to ambient temperature, optionally, removing the mould.

An electrically insulating barrier is formed between the electrode and the counter electrode, preventing the migration of the active components out of the desired zone.

The electrically insulating zone, made of one of the electrically insulating materials cited above, adheres perfectly to the body area, in particular to the skin, at its contact surface. This adhesion ensures the absence of moisture or air between the contact surface with the skin. Furthermore, once the active components located between the electrode or the counter electrode and the electrically insulating zone are deposited at the surface of the skin, these components do not intermingle in the neighbouring deposition zone. The active components therefore remain concentrated on the body area for which they are intended. This concentration improves the penetration of the components into the skin via a two-fold mechanism: occlusion and iontophoresis.

The invention also relates to a cosmetic method comprising the use of a device as defined above.

This method may be a method for cleansing the skin, especially that of the face. The electric current may promote the extraction of one or more species from the skin, where these species are to be eliminated or help to convey away, in their migration, one or more compounds to be eliminated.

The compounds extracted from the skin may, for example, be impurities, ions, peptides, proteins, amino acids, polysaccharides, residues of makeup or deposits of dust.

The compounds extracted from the skin may also be residues of a composition previously applied, for example by a mask as defined above.

The compounds extracted from the skin may or may not be charged. When these compounds are charged, they may have a polarity opposite to that of the electrode to which they are attracted.

The invention may be better understood from reading the following description of the non-limiting implementation example thereof, and also from examining the attached drawing, in which:

DESCRIPTION OF THE FIGURES

Referring to FIGS. 1 and 2, the end piece comprises an application member 6 intended to equip a hand piece 8 of the iontophoresis device 20. The application member 6 comprises an electrode 1 and a counter electrode 2. The electrode 1 and the counter electrode 2 are separated from one another by an electrically insulating zone 3. The iontophoresis device 20 may optionally comprise one or more supplemental modules 14 chosen from a light source, a heat source, a vibration source, or a combination thereof.

Referring to FIG. 3, the end piece includes an application member 6 in the form of a ball rotatable around a rotation axis (X). The application member includes an electrode 1, a counter electrode 2, and an insulating zone 3.

Referring to FIG. 4, the iontophoresis device may include a power source 10, which may be a battery, electrically connected to the application member 6, and a switch 12 configured to control current flow between the power source 10 and the application member 10.

The electrically insulating zone 3 is formed of a polymeric material selected from those listed in the table below.

| Polymeric material | Commercial name | Producer |
|---|---|---|
| HDPE | DOW ™ | DOW |
| LDPE | Elite ® | DOW |
| Polypropylene | Velvex ™ | Styron |
| Polybutadiene | Arinte ® | DSM |
| PET | Rynite ® | DuPont |
| Polystyrene | Styrosolution ®PS | Styrosolution |
| ABS—acrylonitrile butadiene styrene terpolymer | Sicoflex ® | Ravago |
| PMMA | Altuglas ® PMMA | Altuglas International-Arkema |
| PVC | S-58-02 | Shin Etsu |
| Silicones | Tego ® RC Silicones | Evonik Industries |
| TPE | Enflex ® | Ravago |
| TPU | Irogran ® | Huntsman |
| Thermoplastic polyester elastomer | Hytrel ® | DuPont |

The electrically insulating zone 3 forms a bar between the electrode 1 and the counter electrode 2. This bar is defined by:

a height h greater than the thickness e of the electrode and of the counter electrode, a width $L_2$ equal to the distance $L_1$ between the electrode and the counter electrode.

In this example, the length of the wall is equal to the length of the electrode and of the counter electrode.

Figure 1:
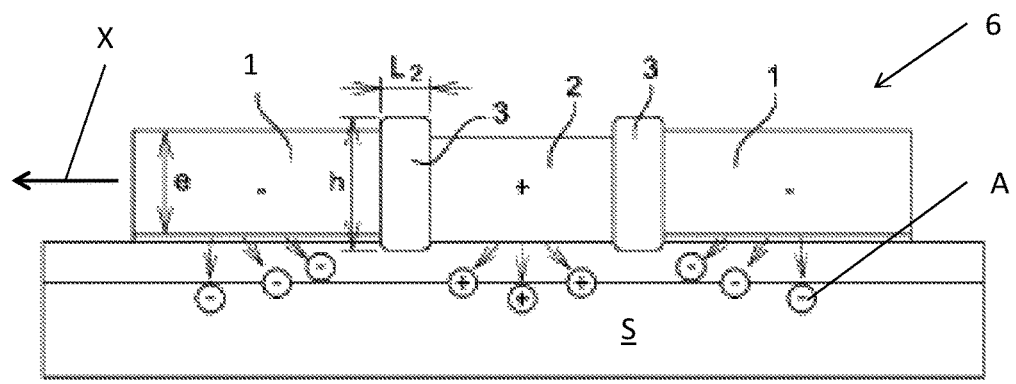
FIG. 1 represents a partial and schematic cross-sectional view of an end piece according to the invention.
Figure 2:
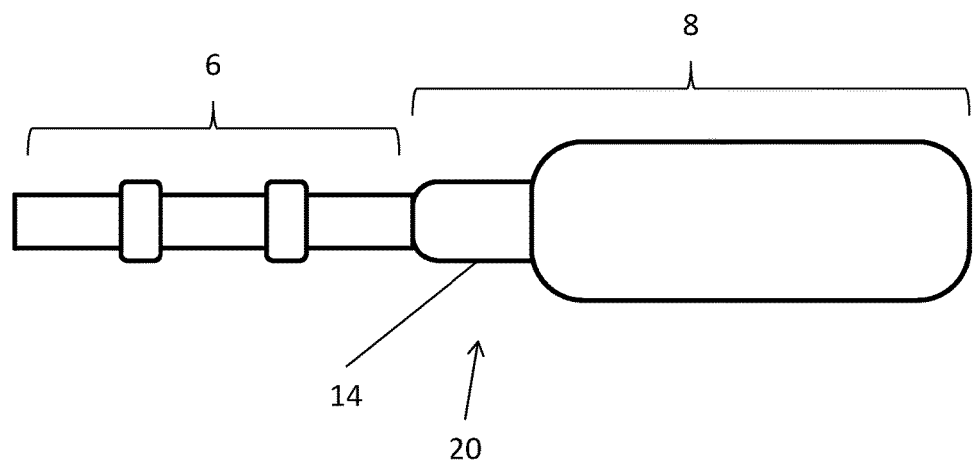
FIG. 2 is a schematic view of an iontophoresis device 20 including the end piece of FIG. 1.
Figure 3:
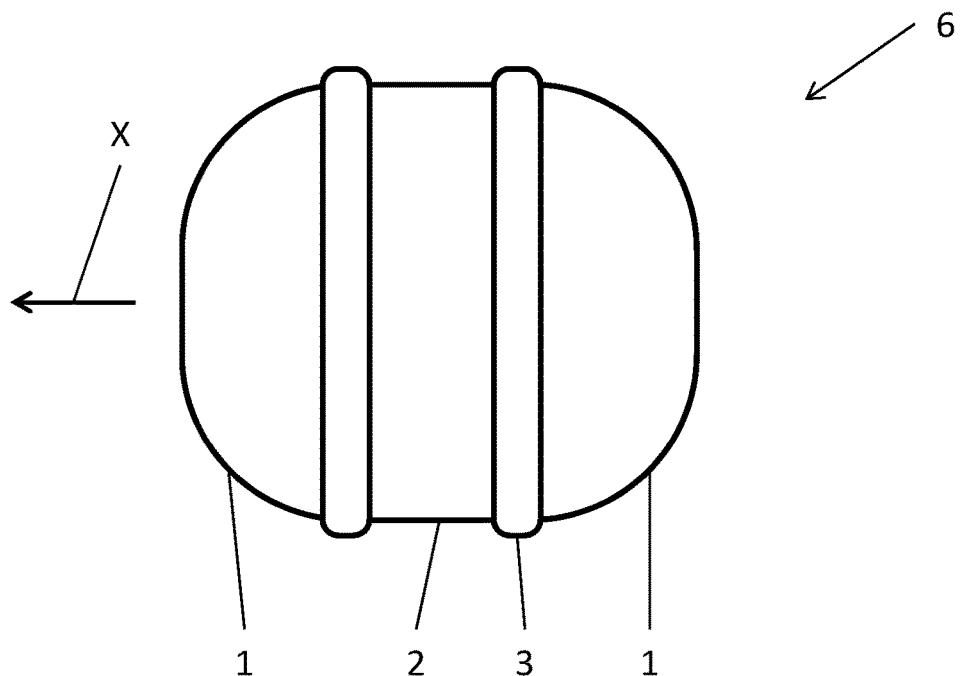
FIG. 3 is a partial and schematic cross-sectional view of an end piece having a ball configuration.
Figure 4:
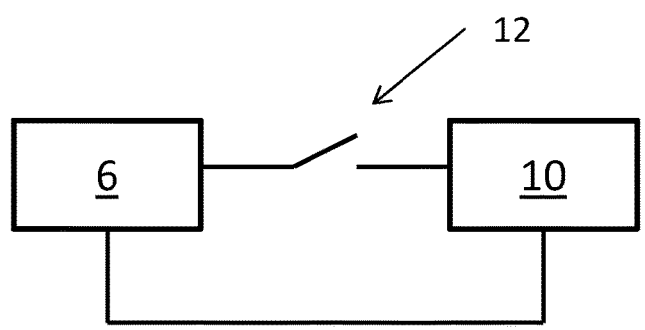
FIG. 4 is a circuit diagram showing electrical connections of the device 20.

FIG. 1 illustrates the paths of the active agents A located close to the electrodes that have the same charge. It is observed that they are repelled towards the skin S and that they do not pass directly towards the other electrode. Thus, the quality of the cosmetic treatment is improved.

The present invention has been described with reference to a particular embodiment, illustrated in FIG. 1, and with reference to a particular example, but it is understood that other variants may be envisaged by a person skilled in the art, in particular the number and types of electrodes may vary and arrangements other than those described may be envisaged in order to form appliances according to the invention. In particular, the shape of the end piece may vary or the position of the electrodes and the counter electrode. Similarly, the geometry or the composition of the electrically insulating zone 3 may vary.

Preferably, the application member of the end piece can rotate about a rotation axis (X).

More preferably, the application member of the end piece is a ball.

More preferably still, the application member comprises at least one relief.

The invention claimed is:

1. An application member configured to be equipped as an end piece of a device for cosmetic treatment of keratin materials with an electric current, the application member comprising:
an electrode;
a counter electrode; and
an electrical insulator separating the electrode and the counter electrode,
wherein the application member is configured to rotate about a rotation axis, and
wherein a thickness of the electrical insulator, taken in a direction perpendicular to the rotation axis, is greater than a thickness of the electrode and a thickness of the counter electrode, taken in a direction perpendicular to the rotation axis, such that the electrical insulator forms a wall that extends from an outer surface of the application member, beyond the electrode and the counter electrode.

2. The application member of claim 1, wherein:
the electrode and the electrical insulator are disposed on a first side of the counter electrode; and
the application member further comprises a second electrode and a second electrical insulator disposed between the second electrode and a second side of the counter electrode.

3. The application member of claim 1, wherein at least one of the electrode, the counter electrode, or the application member is a ball.

4. The application member of claim 1, wherein the wall is configured to prevent the diffusion of a cosmetic composition between the electrode and the counter electrode.

5. The application member of claim 1, wherein the electrical insulator has an electrical conductivity of less than $10^{-6}$ S·m$^{-1}$ and/or a relative permittivity of greater than 0.5.

6. The application member of claim 1, wherein the surface of the application member comprises at least one relief.

7. The application member of claim 1, wherein the electrical insulator comprises a material selected from electrically insulating polymers or electrically insulating ceramics.

8. The application member of claim 1, wherein the electrical insulator comprises an electrically insulating material selected from a thermoplastic material, a thermosetting material, a silicone material, a thermoplastic elastomeric material, a polyester-based or polyether-based thermoplastic polyurethane, or a PVC-based thermoplastic elastomer.

9. The application member of claim 1, wherein the application member comprises a plurality of electrical insulators, each electrical insulator separating adjacent portions of the electrode and the counter electrode.

10. An iontophoresis device comprising:
an application member comprising:
an electrode;
a counter electrode; and
an electrical insulator separating the electrode and the counter electrode;
a hand piece connected to the application member; and
a power supply configured to provide an electrical current between the electrode and the counter electrode of the application member,
wherein the application member is configured to rotate about a rotation axis, and
wherein a thickness of the electrical insulator, taken in a direction perpendicular to the rotation axis, is greater than a thickness of the electrode and a thickness of the counter electrode, taken in a direction perpendicular to the rotation axis, such that the electrical insulator forms a wall that extends from an outer surface of the application member, beyond the electrode and the counter electrode.

11. The device of claim 10, wherein the power supply is configured to selectively change the polarity of the current provided between the electrode and the counter electrode.

12. The device of claim 10, wherein the power supply is configured to provide a sequential current between the electrode and the counter electrode of the application member.

13. The device of claim 10, wherein the power supply is configured to deliver a current density ranging from 0.01 mA/cm$^2$ to 0.500 mA/cm$^2$ to a keratin material in contact with the application member.

14. The device of claim 10, further comprising a heat source configured to heat an external surface of the application member, a keratin material treated by the device, or a combination thereof.

15. The device of claim 14, wherein the heat source comprises a heating resistor, a thermoelectric element, or an infrared source.

16. The device of claim 10, further comprising a light source configured to illuminate a keratin material treated by the device.

17. The device of claim 10, further comprising at least one reservoir comprising a cosmetic composition.

18. A cosmetic treatment method comprising:
providing an iontophoresis device comprising:
an application member comprising:
an electrode,
a counter electrode, and
an electrical insulator separating the electrode and the counter electrode;
a hand piece connected to the application member; and
a power supply configured to provide an electrical current between the electrode and the counter electrode of the application member;
applying an electric current to a keratin material using the application member; and
optionally applying a cosmetic composition to the keratin material prior to or during the application of the electric current,
wherein the application member is configured to rotate about a rotation axis, and
wherein a thickness of the electrical insulator, taken in a direction perpendicular to the rotation axis, is greater than a thickness of the electrode and a thickness of the counter electrode, taken in a direction perpendicular to the rotation axis, such that the electrical insulator forms a wall that extends from an outer surface of the application member, beyond the electrode and the counter electrode.

* * * * *